United States Patent [19]

Nakajima et al.

[11] Patent Number: 5,750,406
[45] Date of Patent: May 12, 1998

[54] ENVIRONMENT MONITORING TEST PIECE AND TEST METHOD

[75] Inventors: Eiichi Nakajima; Yasuo Udoh; Tsutomu Iikawa; Toshisuke Kitakohji; Teruo Motoyoshi; Takashi Furusawa; Shiori Yamazaki; Masao Nakayama; Michiko Satoh; Shigeru Fukushima; Mayumi Itabashi, all of Kawasaki, Japan

[73] Assignee: Fujitsu Limited, Kawasaki, Japan

[21] Appl. No.: 432,259

[22] Filed: May 1, 1995

Related U.S. Application Data

[63] Continuation-in-part of Ser. No. 178,357, Jan. 4, 1994, which is a continuation-in-part of Ser. No. 140,153, Nov. 4, 1993, abandoned.

[51] Int. Cl.⁶ .................................................. G01N 17/04
[52] U.S. Cl. ........................... 436/116; 436/111; 436/119; 422/53
[58] Field of Search ................................ 422/53; 436/6, 436/116, 111, 119

[56] References Cited

U.S. PATENT DOCUMENTS

| | | | |
|---|---|---|---|
| 3,164,004 | 1/1965 | King | 73/23 |
| 3,329,004 | 7/1967 | King, Jr. | |
| 4,099,922 | 7/1978 | Yasuda et al. | 23/254 E |
| 4,235,098 | 11/1980 | Tisch | |
| 4,508,624 | 4/1985 | Nagata | 210/658 |
| 4,759,210 | 7/1988 | Wohltjen | |
| 4,869,874 | 9/1989 | Falat | 422/53 |
| 5,208,162 | 5/1993 | Osborne et al. | 436/6 |

FOREIGN PATENT DOCUMENTS

| | | |
|---|---|---|
| 0 120 203 | 10/1984 | European Pat. Off. |
| 17 73 968 | 8/1968 | Germany |
| 21 51 693 | 10/1971 | Germany |
| 32 09 013 | 10/1983 | Germany |
| 63-177737 | 11/1988 | Japan |
| 63-305232 | 12/1988 | Japan |
| 64-072062 | 3/1989 | Japan |
| 1-160349 | 11/1989 | Japan |
| 1-290552 | 11/1989 | Japan |
| 3-089162 | 4/1991 | Japan |
| 3-076148 | 7/1991 | Japan |
| 3-296647 | 12/1991 | Japan |
| 1 223 132 | 2/1971 | United Kingdom |
| 1 515 421 | 6/1978 | United Kingdom |
| 1 527 302 | 10/1978 | United Kingdom |
| 2 158 816 | 11/1985 | United Kingdom |

OTHER PUBLICATIONS

*Patent Abstracts of Japan*, vol. 13, No. 138 (P–852) Apr. 6, 1989 & JP–A–63 305232 (Fujitsu Ltd) Dec. 13, 1988.

*Primary Examiner*—Lyle A. Alexander
*Attorney, Agent, or Firm*—Staas & Halsey

[57] ABSTRACT

There is provided a test piece by which $NO_x$ present in an environment may be visually observed apart from the influence of other gases, and with which qualitative and quantitative analysis may be performed. The test piece has a layered structure prepared by vacuum deposition a metal thin-film (Ag, Pt, Au, etc.) on a metal substrate (Cu, Zn, etc.). The rough amounts of $NO_x$, $SO_x$ and $NH_3$ in the environment are determined on the basis of the corrosion products (nitrates, etc.) produced when $NO_x$, $SO_x$ and $NH_3$ are collected after the test piece has been exposed to the environment for a prescribed period of time.

18 Claims, 9 Drawing Sheets

ANODE: BASE METAL SUCH AS Cu, Zn, Mg
CATHODE: NOBLE METAL SUCH AS Ag, Pt, Au

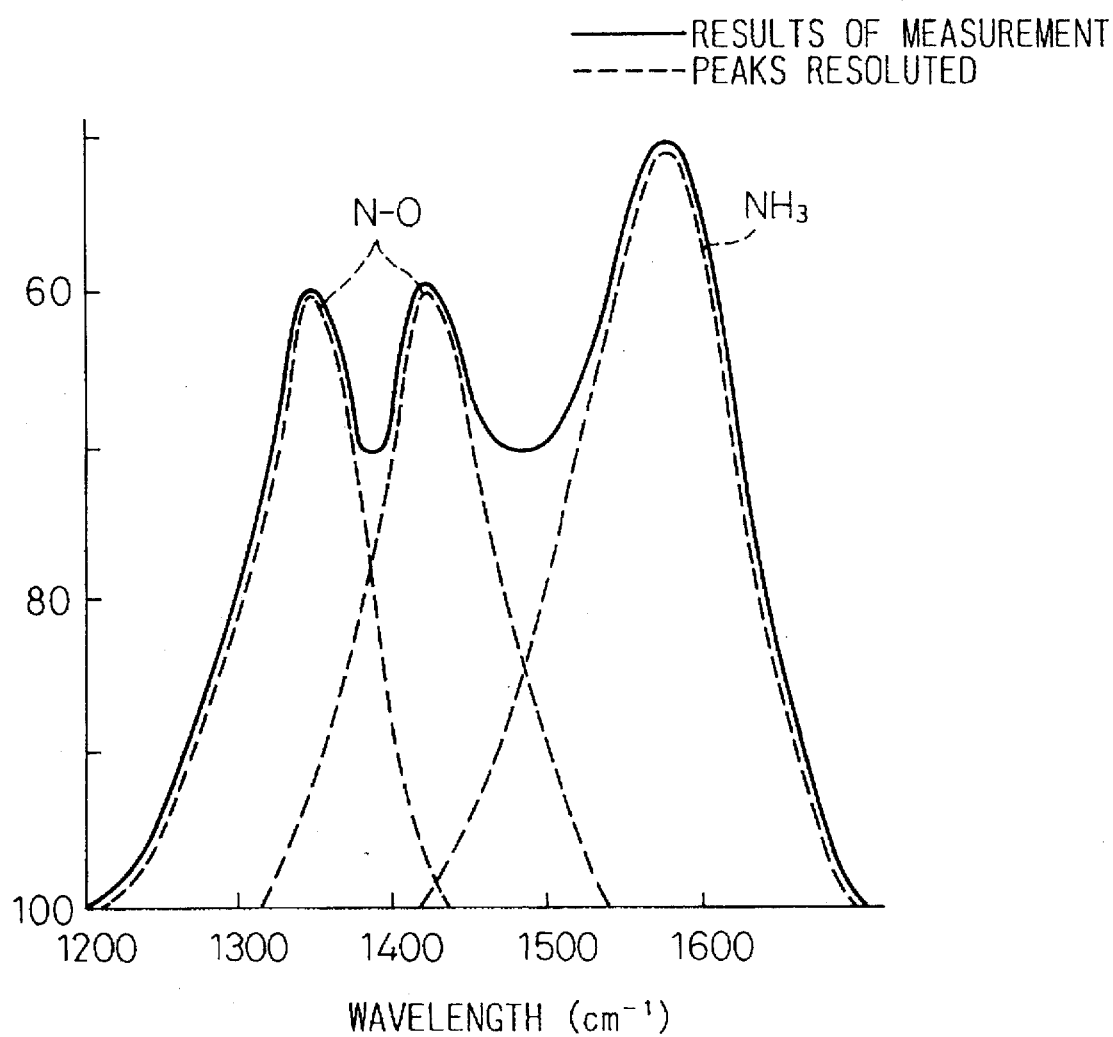

ENVIRONMENT MONITORING TEST PIECE AND TEST METHOD

CROSS REFERENCE TO RELATED APPLICATIONS

The present application is the continuation-in-part application of U.S. Ser. No. 08/178,357 filed on Jan. 4, 1994, which is in turn the continuation-in-part application of U.S. Ser. No. 08/140,153 filed on Nov. 4, 1993 now abandoned.

BACKGROUND OF THE INVENTION

1. Field of the Invention

The present invention relates to an environment monitoring test piece and to an environment monitoring method which employs it. More specifically, it relates to an environment monitoring test piece with which nitrogen oxides ($NO_x$) present in the atmosphere may be collected and the general amount of $NO_x$ present in the environment analyzed and assessed by the "change in color" and "shade of color" of the test piece, and with which the detailed concentration of $NO_x$ may be known by using an appropriate analyzer.

2. Description of the Prior Art

With the continued downsizing of electronic devices such as personal computers, word processors, telephones, POSs, ATMs, and the like in recent years, the wiring pitches of wiring boards are becoming smaller, and the packaging density of connectors, etc. is increasing. Recently, these electronic devices are increasingly being used in environments which are either outdoors or essentially outdoors, such as under eaves. Yet it is thought that such devices are usually designed under the assumption that they will be moved around in office environments, and consequently there is concern that they are not suited to harsh environments.

In addition, electric machines which are used outdoors, such as vending machines, radio equipment and various types of control equipment, are also exposed to environments which become harsher with deteriorating environmental conditions, and are thus prone to a wide range of damage.

An especially important issue is the problem of environmental pollution due to $NO_x$, $CO_x$ and $SO_x$ present in the atmosphere. $NO_x$, in particular, is generated in exhaust from automobiles and factories, and in contrast to the concentration of $NO_x$ (including $NO_2$+NO) which is on the order of a few ppb in nature, the concentration in large cities reaches a maximum of 100 ppb, with an average of 50 ppb, and is thus becoming a major social issue.

The present applicant has developed and disclosed a method capable of easily monitoring average concentrations of harmful gases such as $H_2S$, $SO_x$, $NO_x$ and Cl gases and humidity at any desired site, in the already disclosed Japanese Unexamined Patent Publication No. 63-305232 and U.S. patent application Ser. No. 08/140,153, filed Nov. 4, 1993, now abandoned in favor of Ser. No. 08/178,357, filed Jan. 4, 1994.

According to this method, metal pieces of various types such as described in the above-mentioned applications are placed in appropriate cases and allowed to stand for 30 days in an environment in which harmful gases are present. As a result, specific gases react with specific metals, such as hydrogen sulfide with Ag and moisture with Fe. When this occurs, the corrosion products generated with each of the metals exhibit characteristic colors. For example, Ag exposed to an environment containing hydrogen sulfide turns blue, while Fe exposed to a humid environment turns brown. Also, although the shades of the colors depend on the concentrations in the environment, there are no basic changes in the colors themselves. That is, Ag exposed to an environment with a low concentration of hydrogen sulfide still turns blue despite the low concentration.

Thus it is possible to determine the types and rough concentrations of gases in an environment based on changes in the colors of the metals and the shades of the colors, without having any special knowledge.

Nevertheless, of the types of gases mentioned above, although the collection of $NO_x$ is possible with the materials disclosed in U.S. patent application Ser. No. 08/140,153, the purpose of assessing environments based on color changes of the test pieces is not satisfactorily achieved. Furthermore, the methods of working powder mold materials and single metal plates involve complicated process steps, and it has been somewhat difficult to achieve stable large-scale production. In addition, the working of each piece requires time and is rather costly.

BRIEF SUMMARY OF THE INVENTION

Consequently, it is an object of the present invention to provide a test piece for environmental measurement which allows rough detection of $NO_x$ on the basis of color change and which may be easily manufactured, as well as a testing method which employs it.

In order to realize the object of "environmental assessment by color changes", the present invention is carried out by layering a metallic inorganic thin-film on a metal substrate.

BRIEF DESCRIPTION OF THE DRAWINGS

FIG. 11 illustrates the principle of the peak resolution method.

DETAILED DESCRIPTION OF THE INVENTION

Figure 1A:
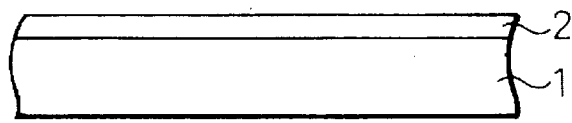
FIGS. 1A, 1B and 1C are illustrations of a test piece for environmental measurement and the operating principle thereof.

The layering is performed on a substrate consisting of a metal plate of Cu, Zn or the like which is capable of collecting first $NO_x$, and also $SO_x$, $NH_3$, etc., and laying thereon a metal such as Ag or Pt, and particularly one of the noble metals such as Ag, Pt, Au, etc., by vacuum deposition. The metal plate and the metal thin-film should be made of different metals. The method of vacuum deposition may be vapor deposition, sputtering or CVD.

When a noble metal is contacted with Cu, Zn, Mg or another base metal, gases such as $NO_x$, $SO_x$, $NH_3$ or their mixtures with water act as electrolytes (acids or bases), to generate an electrochemical reaction with the base metal as the anode and the noble metal as the cathode, resulting in an improved ability to collect the $NO_x$, $SO_4$, $NH_4$, etc. by the Cu, Zn, Mg or other base metal.

The chemical properties and ionization series of some metals are provided below for reference.

corrosion product 4 containing the nitrates produced by the respective metals (copper nitrate and silver nitrate) interferes to cause the appearance of a characteristic color. This is believed to correspond to the electrochemical reaction shown in FIG. 1C. Consequently, any metal may be used for the purpose of the present invention so long as it serves as a metal electrode which undergoes an electrochemical reaction with nitric acid as the electrolyte, to produce a colored reaction product (nitrate).

The metal thin-film is gas permeable, with a thickness of 400 nm or less, preferably in the range of 20–400 nm, and more preferably in the range of 100–200 nm.

This environment monitoring test piece is placed in an environment to be measured, and after a certain period of time, the test piece is examined for corrosion products produced by $NO_x$, or $SO_x$, $NH_3$, etc. For the purpose of the present invention, the rough i.e., approximate amounts of $NO_x$, or $SO_x$, $NH_3$, etc. in the environment may be known based on the color change of the test piece, but it is also possible to conduct a more precise analysis of the amounts

| | Metal chemical properties and ionization series | | | | | | | | | | | | | |
|---|---|---|---|---|---|---|---|---|---|---|---|---|---|---|
| Metal | K | Ca | Na | Mg | Al | Zn | Fe | Ni | Sn | Pb | (H) | Cu | Hg | Ag Pt Au |
| Reaction with air | | | | | | | | | | | | | | |
| Room temp. | Oxidized even if in dry air | | | Oxides produced on surface in dry air. Oxidation accelerated in humid air. | | | | | | | | | | Not oxidized |
| High temp. | Vigorous combustion, oxides produced | | | Combustion, oxides produced | | | Only surface oxidized | | | | | | | Not oxidized |
| Reaction with water | Hydrogen generated and hydroxides produced | | | Reaction with water vapor, generating hydrogen and producing oxides | | | No reaction | | | | | | | |
| Reaction with chlorine and dilute sulfuric acid | Hydrogen generated and salt formed (Pb forms insoluble salt and does not react) | | | | | | | | | | | No reaction | | |
| Reaction with nitric acid and hot conc. sulfuric acid | Oxidized ($NO$, $NO_2$, $SO_2$, etc. generated and salt formed) | | | | | | | | | | | | | No reaction |
| Reaction of oxides | Not reduced by hydrogen | | | Reduced by hydrogen | | | | | | | | | | Oxygen released upon heating |

The thin-film obtained by the vacuum deposition method is usually more chemically active than in bulk form, and therefore it is highly gas-adsorbent. Also, since the thin-film form is more porous than the bulk, gases may pervade to the interior of the film structure.

The merit of forming the film by vacuum deposition is that stable, consistent-quality pieces may be produced on a large scale. To cite a familiar example, compact discs produced by vacuum deposition have a cost of at the most a few hundred yen.

Figure 1B:
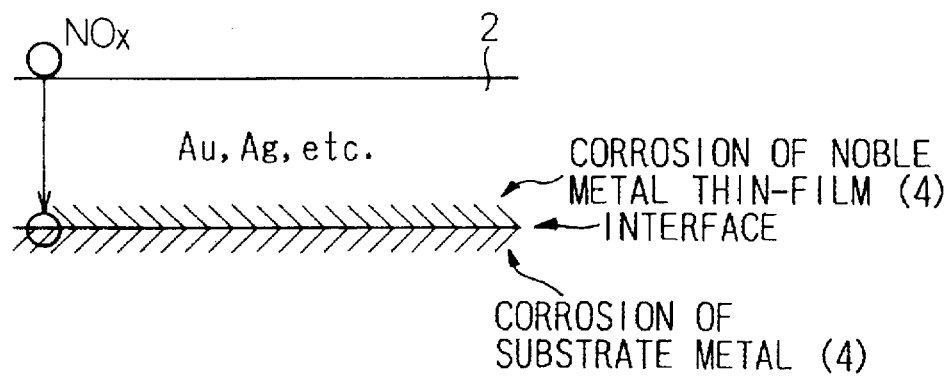
Figure 1C:
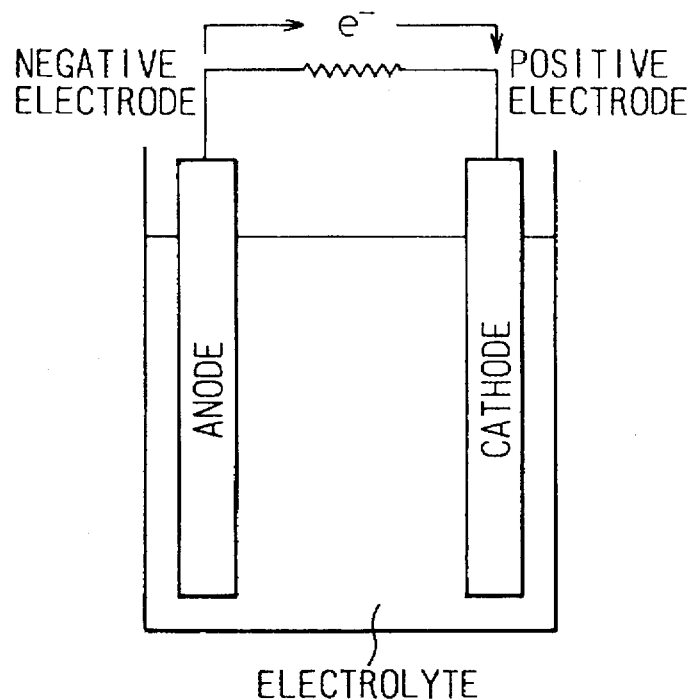

The mechanism of $NO_x$ detection according to this method may be explained as follows. $NO_x$ gas and water, present as humidity, permeate the upper layer thin-film (e.g., Ag) 2 of the metal plate (e.g., Cu) 1 as shown in FIGS. 1A and 1B, and reach the interface while generating nitric acid. Here, as an effect of the present invention, the metal plate and metal thin-film (Cu and Ag) both corrode at their interface due to the electrochemical action, etc. resulting from the contact of the two metals, and a color change of the of corrosion products by, for example, a Fourier Transform Infrared Spectroscopy Reflection Absorption Spectroscopy (FT-IR RAS analysis).

EXAMPLE 1

A test piece having the construction shown in FIG. 1A was prepared. The substrate used was 99.99% purity oxygen-free copper worked to 40×5 mm×0.5 t.

Silver was laminated on this substrate to a thickness of 2000 Å by electron beam vacuum deposition to complete the test piece Cu/Ag.

Also, FT-IR RAS was used to confirm the presence of nitric acid in the corrosion product obtained by reaction with $NO_x$.

The environment-simulating apparatus was an suitable container designed to allow the introduction of gases and humidity. The concentrations were adjusted by depressurization of the cylinder gas pressure, and by using a mass flow controller and dilution apparatus.

The prepared test piece was placed in the environment-simulating apparatus and taken out every week (168 h) for analysis by color change and FT-IR RAS. The environment in the environment-simulating apparatus was adjusted to 50 ppb of $NO_2$ and 90% relatively humidity, based on a standard outdoor environment.

The results confirmed a gradual change of the test piece from a silver color to a yellow-green color with the passage of time.

Figure 2:
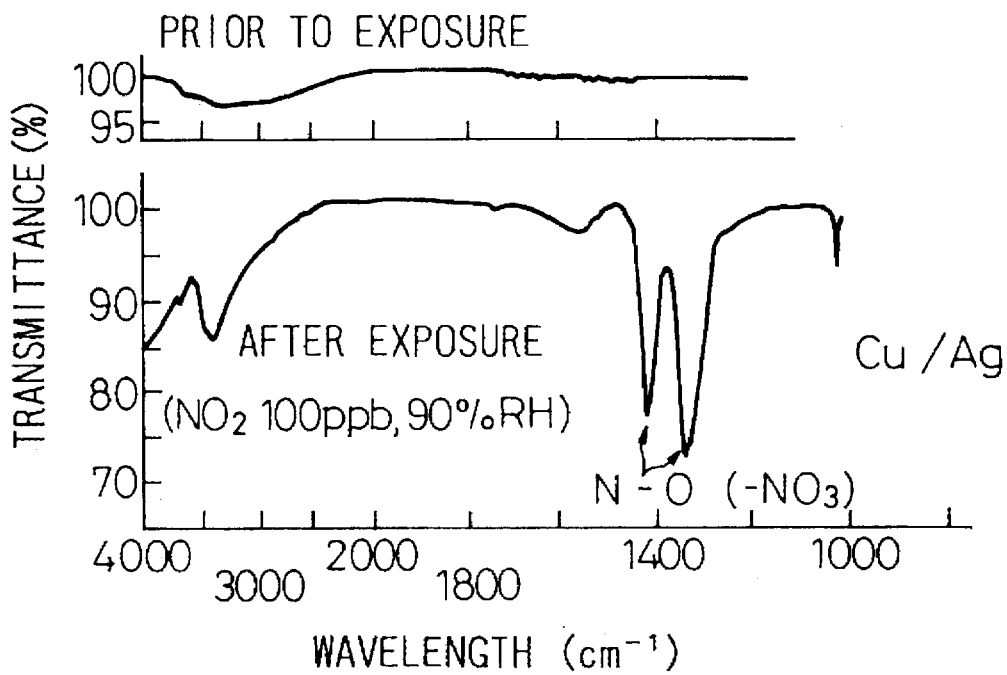
FIG. 2 shows the results of FT-IR RAS analysis of an embodiment of a Cu/Ag test piece.

FIG. 2 shows the results of FT-IR RAS analysis of a test piece with a Ag film thickness of 2000 Å exposed to the environment for 4 weeks (672 h) as an example. The results confirm that the test piece collected $NO_2$ and contained a salt of $HNO_3$ as a corrosion product, seen at 1420 and 1340 $cm^{-1}$.

Figure 3:
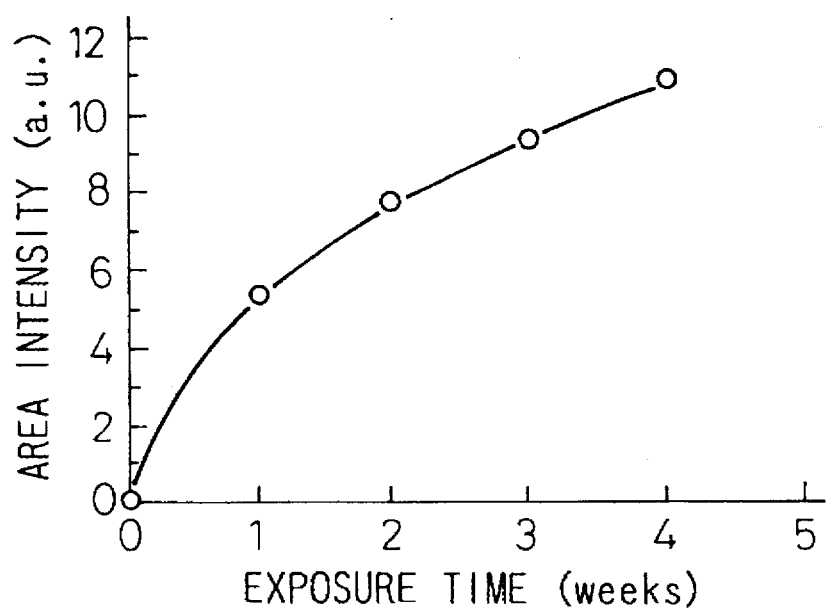
FIG. 3 shows a plot of the area intensity against exposure time at an absorbance of 1200–1600 cm$^{-1}$ according to the embodiment.

From the results of the above-mentioned qualitative analysis, the absorbance at 1200–1600 $cm^{-1}$ corresponding to the $HNO_3$ salt of FIG. 2 was integrated to obtain the area, which was then converted to area intensity as shown in FIG. 3. These results show an increase in area intensity with time, and therefore a quantitative relationship.

Figure 4:
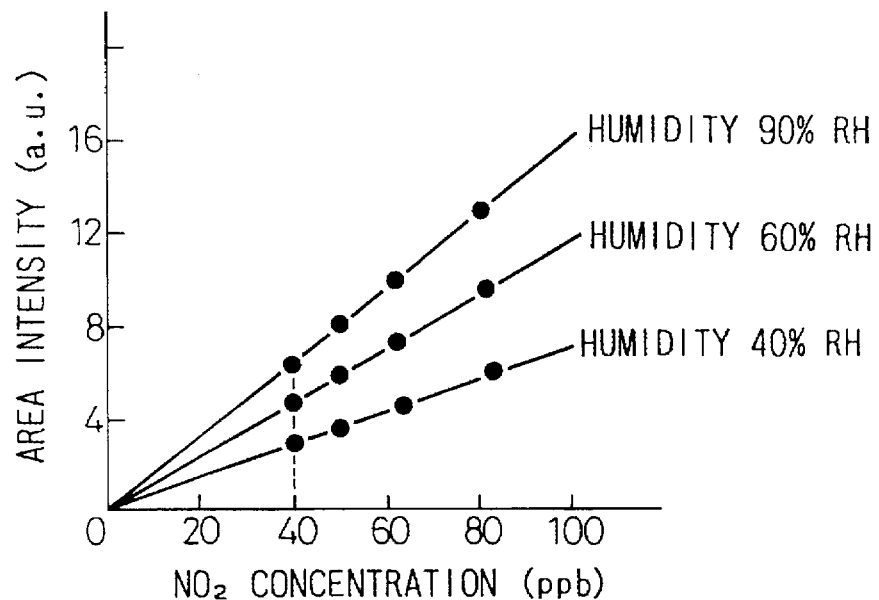
FIG. 4 shows the relationship between $NO_x$ concentration in the environment and area intensity according to FT-IR RAS analysis.

FIG. 4 shows the relationship between $NO_2$ and the area intensity. This is an analytical curve obtained by plotting the relationship between the $NO_2$ concentration and the area intensity found by exposing test pieces in the above-mentioned environment-simulating apparatus at a constant concentration for a constant period of time.

Figure 5:
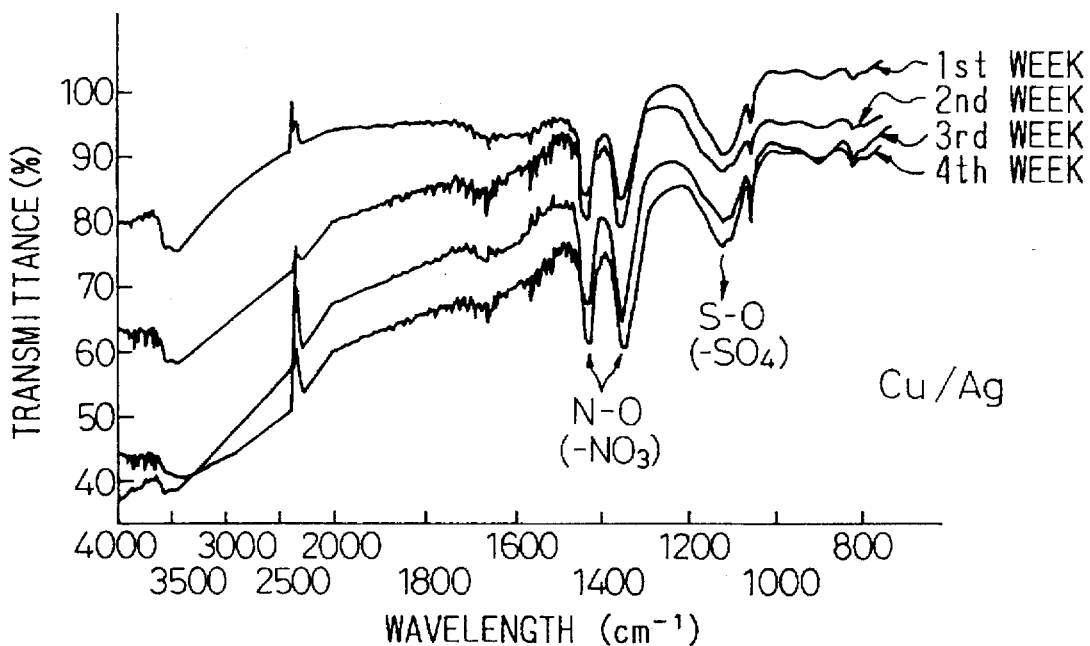
FIG. 5 shows the results of FT-IR RAS analysis of a Cu/Ag test piece exposed to a field environment as in Example 1.

FIG. 5 shows the results of FT-IR RAS analysis of the same type of environment test piece exposed to the inside of Fujitsu Factory in Nakahara Ward, Kawasaki. These results show a peak at 1115 $cm^{-1}$ due to $SO_2$ in the environment, but it is completely separate from the peaks at 1420 and 1340 $cm^{-1}$ due to $NO_2$ and thus presents no obstacle to qualitative or quantitative analysis. Also, in regard to the outward color, the silver color gradually changed to yellow-green with the passage of time, in the same manner as the test piece exposed to the environment-simulating apparatus.

The $NO_2$ concentration was calculated from the analytical curve in FIG. 5 to be about 50 ppb, and this roughly matched the results reported by the City of Kawasaki.

In this manner, the Cu substrate/Ag thin-film allowed visual observation of the presence of $NO_x$, as well as subsequent qualitative and quantitative analysis.

EXAMPLE 2

A test piece was prepared as shown in FIG. 1A. The substrate used was a 99.9% pure Zn plate worked to 40×5 mm×0.5 t.

Gold was laminated on this substrate to a thickness of 1000 Å by vacuum deposition to complete the test piece Zn/Au. The gold material used had a purity of 99.9%, and the degree of vacuum in the apparatus was under $1×10^{-9}$ Pa.

The test piece prepared in this manner was placed in an environment-simulating apparatus and tested in the same manner as in Example 1.

As a result it was found that the test piece lost its metal luster as time progressed, gradually changing color to orange.

Figure 6:
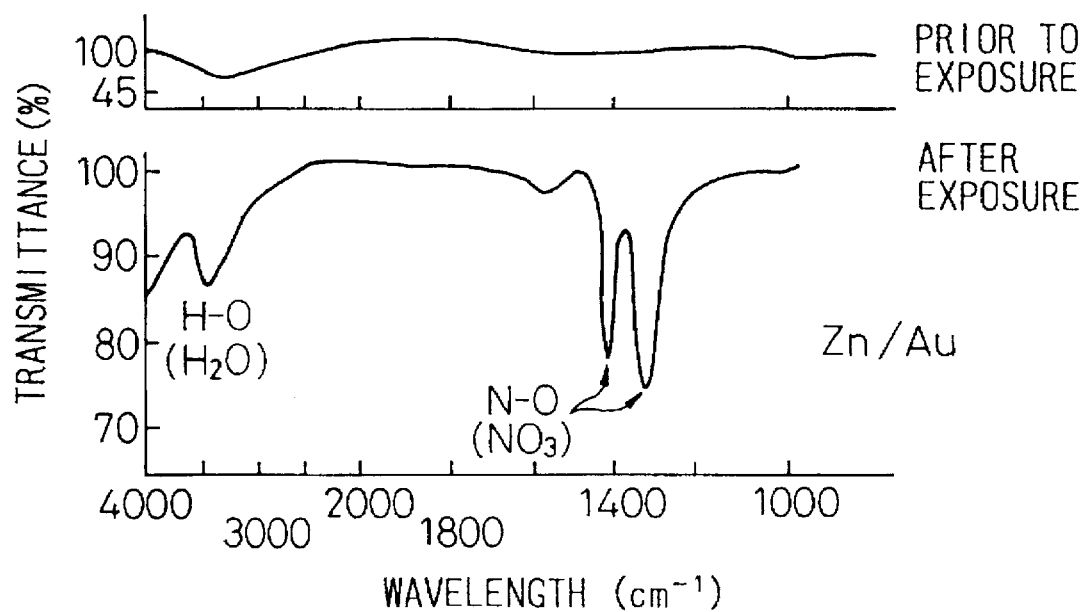
FIG. 6 shows the results of FT-IR RAS analysis of the Zn/Au test piece in Example 2.

FIG. 6 shows the results of analysis by FT-IR RAS. The results confirm that, similar to Example 1, the test piece collected $NO_2$ and contained a $HNO_3$ salt as a corrosion product, seen at 1420, 1340 $cm^{-1}$. The reason for the similar results as Example 1 is believed to be that the obtained corrosion product had the structure $Zn(NO_3)_x$ (x assumed to be 2), which was reflected in the FT-IR RAS analysis by the vibration of the N and O in the $NO_3$.

Figure 7:
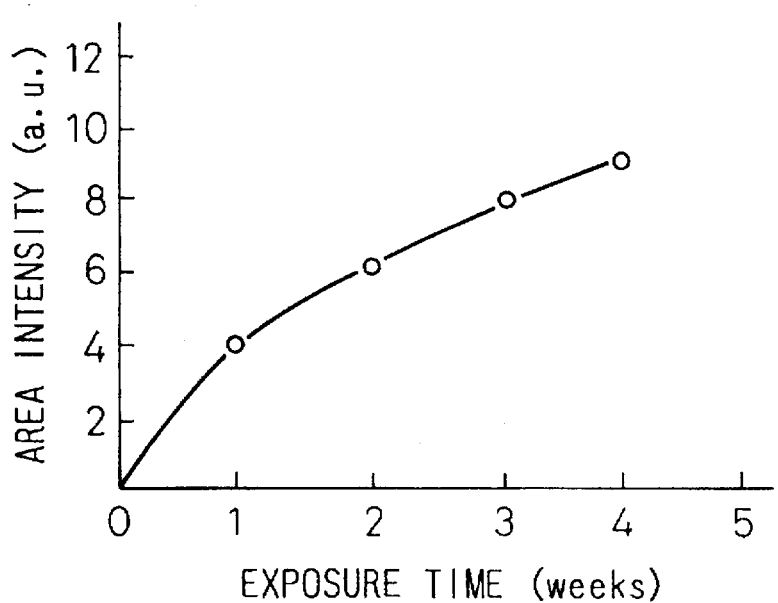
FIG. 7 shows the relationship between exposure time and area intensity for Example 2.

In the same manner as for Example 1, the absorbance at 1200–1600 $cm^{-1}$ corresponding to FIG. 6 was integrated to obtain the area, which was then converted to area intensity as shown in FIG. 7. These results show an increase in area intensity with time, and therefore a quantitative relationship.

Figure 8:
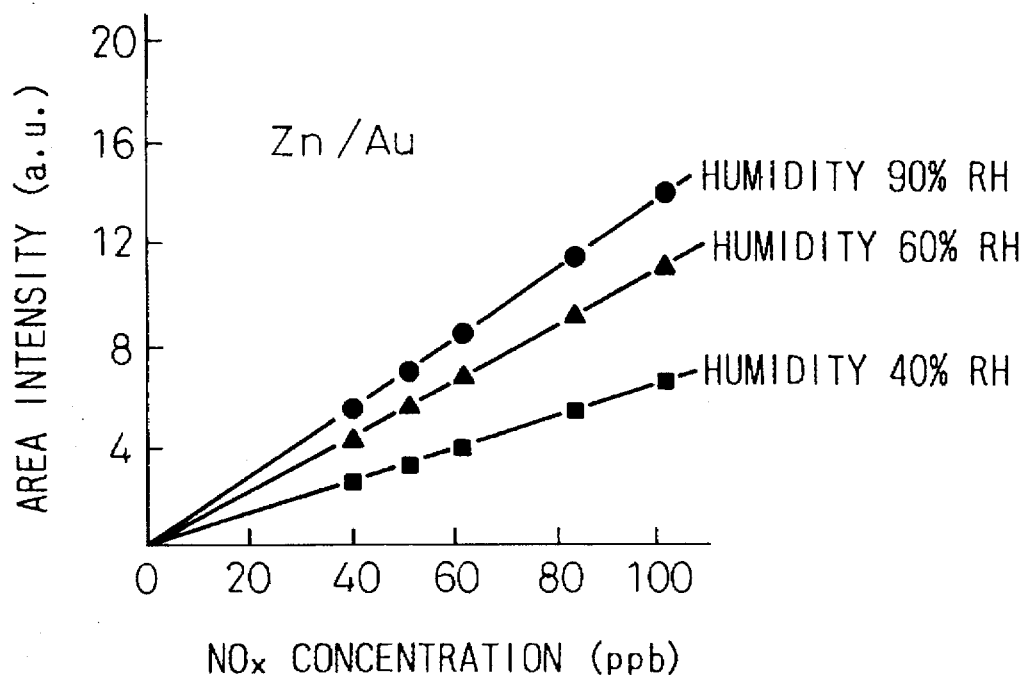
FIG. 8 shows the relationship between $NO_x$ concentration and area intensity for Example 2.

FIG. 8 shows the relationship between $NO_2$ and the area intensity. This is an analytical curve obtained by plotting the relationship between the $NO_2$ concentration and the area intensity found by exposing test pieces in the above-mentioned environment-simulating apparatus at a constant concentration for a constant period of time.

The method described above is the same as employed in Example 1, and similar results were obtained. Therefore, the accuracy of the method was confirmed.

Figure 9:
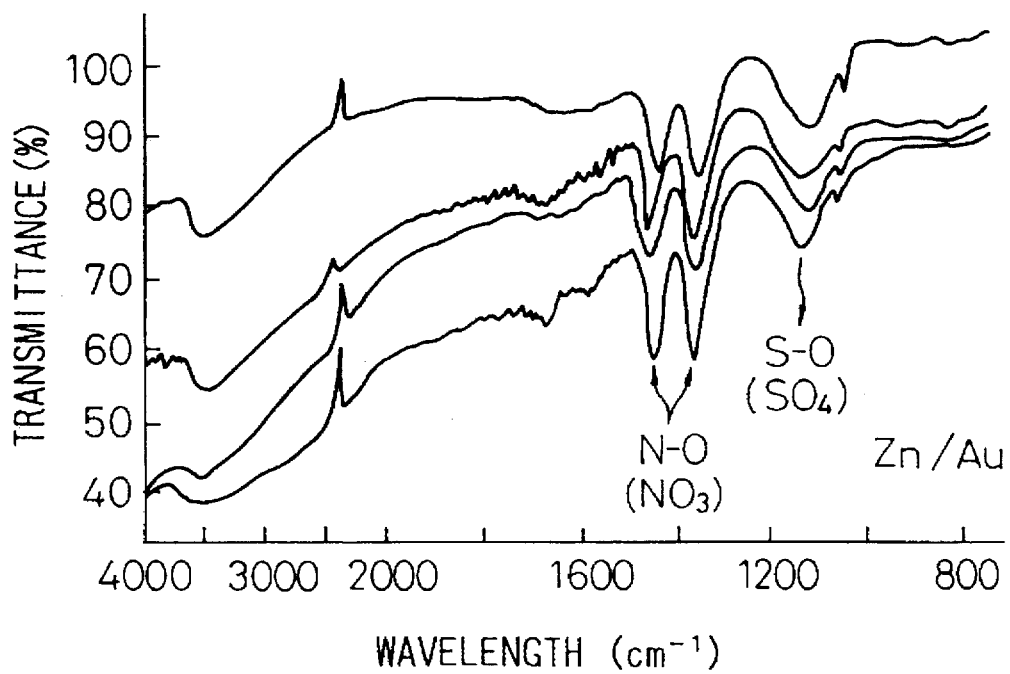
FIG. 9 shows the results of FT-IR RAS analysis of the Zn/Au test piece exposed to a field environment as in Example 2.

FIG. 9 shows the results of FT-IR RAS analysis of the same type of environment test piece exposed for one month at the General Atmospheric Measurement Bureau of the Ota Ward Office in Tokyo (a bureau which measures harmful gases such as $NO_2$ in city streets). The results confirmed a peak in the environment at 1115 $cm^{-1}$ due to $SO_2$, as well as peaks at 1420 and 1340 $cm^{-1}$ due to $NO_2$, similar to Example 1. Also, the outward color changed with the passage of time in the same manner as the test piece exposed to the environment-simulating apparatus, but it differed in this case in that the orange color was lighter.

The $NO_2$ concentration was about 50 ppb, as determined by further inverse calculation from the area intensity obtained by analysis using the analytical curve in FIG. 8 for the Zn/Au test piece, and this roughly matched the data reported by Ota Ward.

Thus, the method allows visual confirmation of the presence of NO in particular, as well as qualitative and quantitative analysis.

EXAMPLE 3

A Cu substrate/Ag test piece also allows simultaneous qualitative and quantitative measurement of $NO_x$, $SO_x$ and $NH_3$ by the method described above.

The simulated environment was set to 50 ppb of $NO_2$ and 40 ppb of $SO_2$ which are the environmental standard limits, and 20 ppb of $NH_3$ which has no environmental standard, and the environment was adjusted to 90% RH. The test piece was exposed to the environment for one month as in the previous example.

Since the test piece produces a complexity of corrosion products in this case, it is somewhat difficult to make a quantitative analysis of the environment based on visual observation. A light blue color change is exhibited here, but for more accurate color discernment colored samples are prepared for the various amounts of each of the three types of gases. However, qualitative and quantitative analysis are possible by FT-IR RAS in the same manner as in the previous two examples.

Figure 10:
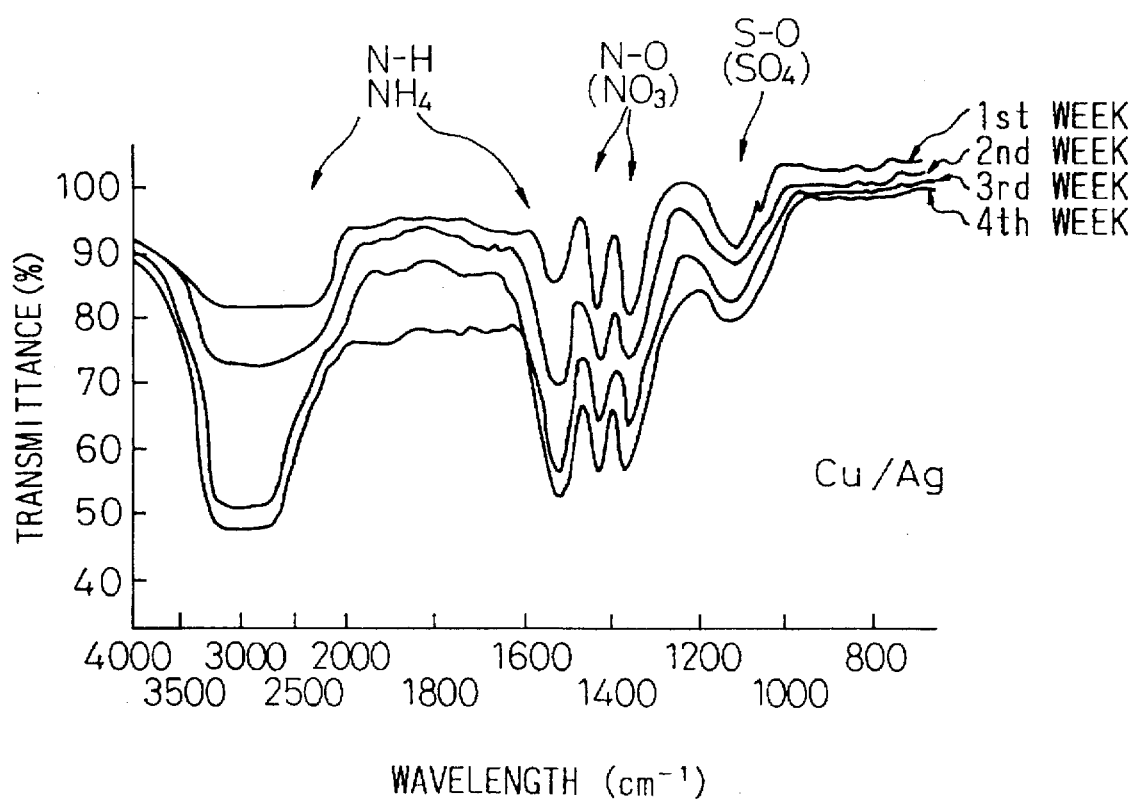
FIG. 10 shows the results of FT-IR RAS analysis of a Cu/Ag test piece exposed to a complex environment as in Example 3.

FIG. 10 shows the results of FT-IR RAS analysis of a test piece taken out once a week during exposure to a simulated environment. It is also understood from these results that simultaneous analysis of $NH_3$, $SO_2$ and $NO_2$ is possible.

In the analysis by FT-IR RAS, the N—O vibration near 1400 $cm^{-1}$ and the N—H vibration near 1500 $cm^{-1}$ are very close, and depending on their amounts they may overlap; however, since overlapping peaks may be resolved by the method of peak resolution, this does not affect the analysis or measurement except in cases where the distinction of the peaks is impossible. FIG. 11 shows an example of this method.

Qualitative analysis of the gases present in the environment is possible by the method described above, while quantitative analysis is also possible by generating an analytical curve corresponding to the peaks.

As mentioned above, by using a noble metal thin-film/Cu substrate test piece or a noble metal thin-film/Zn substrate test piece according to the present invention, it is possible to detect $NO_x$ present in an environment by visual observation, apart from the influence of other gases, and to perform qualitative and quantitative analysis.

Furthermore, the test pieces may be used for distinguishing one gas from other interfering gases by visual observation and analysis.

The use of this type of test piece allows measurement of long-term average concentrations of $NO_x$ at given locations, and it is therefore valuable from the standpoint of knowing states of atmospheric pollution by $NO_x$ which is becoming a major social issue, while its greatest effect is exhibited when applied to the terrestrial environment.

EXAMPLE 4

To determine the structure of the corrosive product which forms on the surface of the test piece shown in Examples 1 to 4, X-ray diffraction analysis was used.

From the result, all samples had the same structure, a mixture of $Cu_2O+Cu_2(OH)_3NO_3+Cu_{15}(SO_4)_4(OH)_{22.6}$.

Figure 12A:
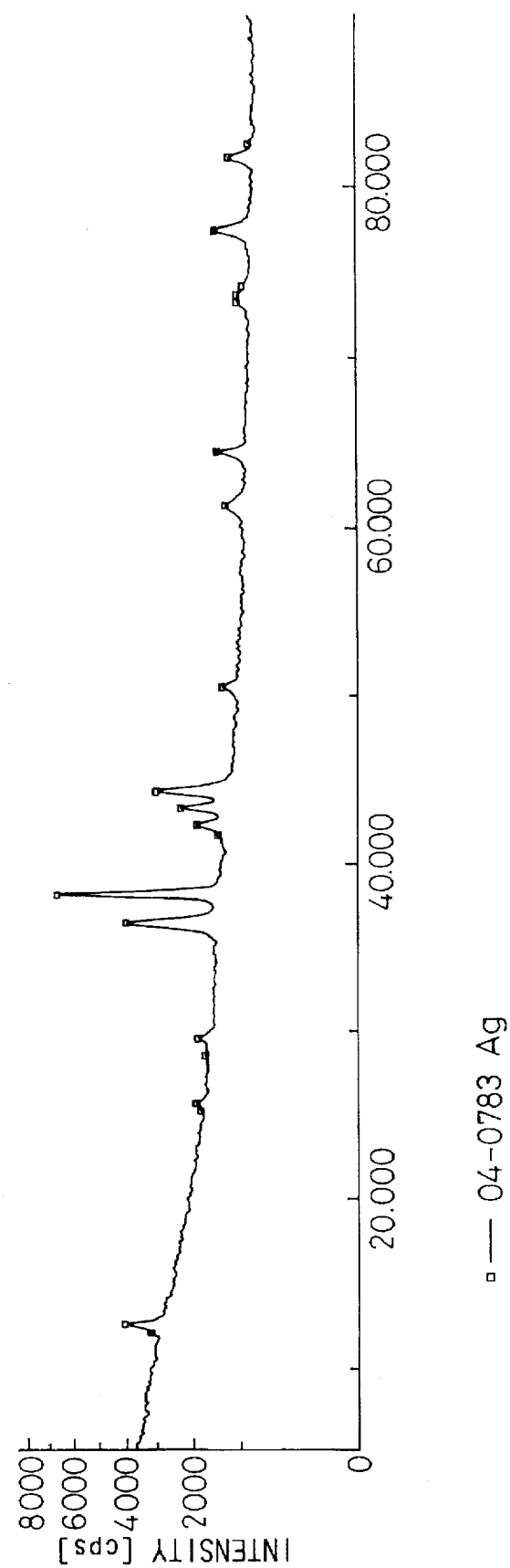
FIGS. 12A and 12B are the X-ray diffraction chart and peak data thereof of the corrosive product formed on the test piece in Examples.
Figure 12B:
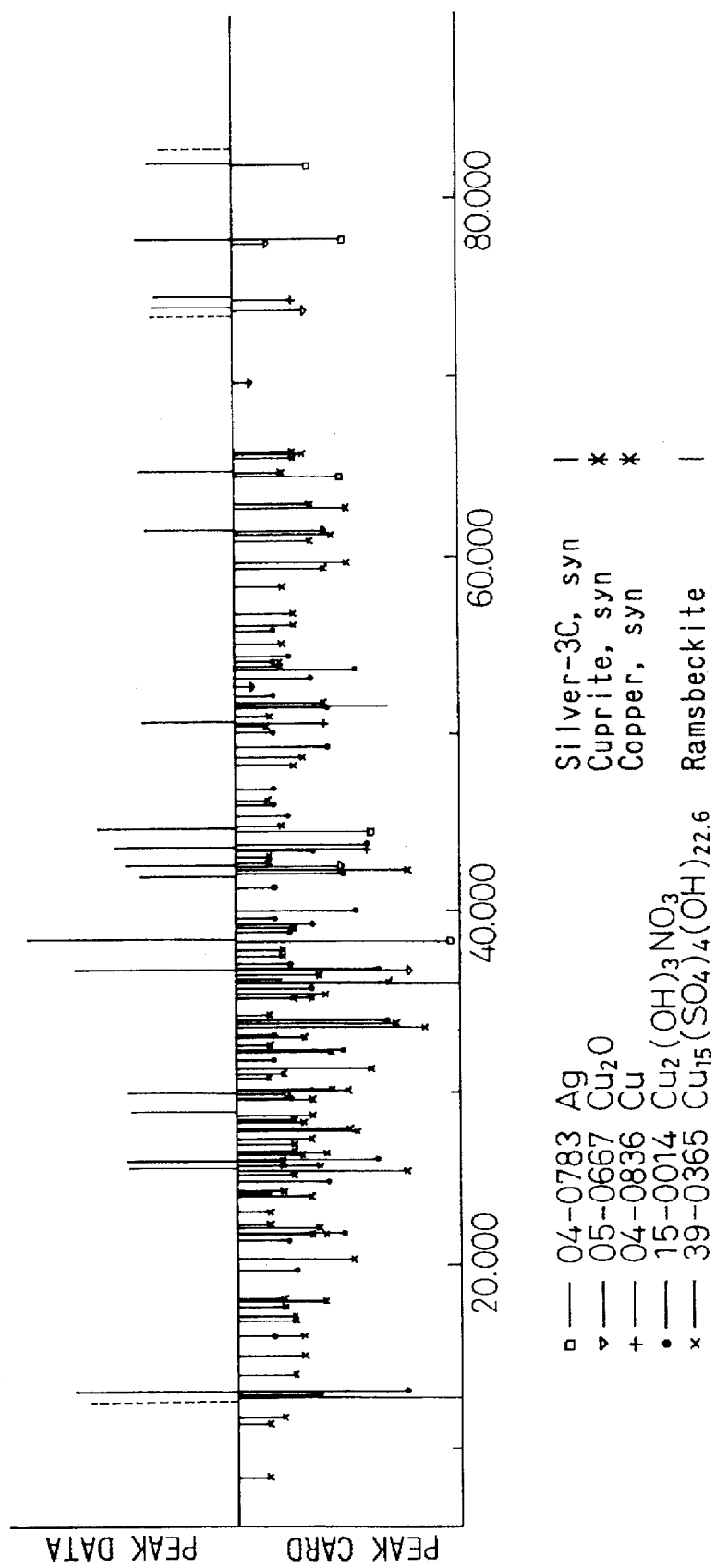

FIGS. 12A and 12B show the X-ray diffraction chart (and peak data thereof). The result of the structure shown above was obtained by comparing the peak chart with the JCPDS data base.

This means that the origin of the corrosive product formed above the test piece corresponds to $NO_x$ (and $SO_x$ gas) that exists in the environment.

This result correspond to the results of FT-IR RAS, shown in the previous examples.

JCPDS data base: a data base which includes about 65000 subjects of X ray-diffraction patterns (mostly inorganic structures).

JCPDS: Joint Committee on Powder Diffraction Patterns.

We claim:

1. An environment monitoring test piece, comprising:
   a layered structure comprising a metal thin-film formed on a metal substrate and defining an interface therebetween, which test piece is to be placed in an environment to be measured thereby to selectively determine an approximate amount of at least one gas, selected from the group consisting of $NO_x$, $SO_x$, and $NH_3$, in the environment based on at least one corresponding corrosion product resulting from the interaction of said selected gas from the environment with said test piece after a prescribed period;
   said metal substrate comprising at least one metal selected from the group consisting of Cu, Cu alloy, Zn, and Zn alloy; and
   said metal thin-film comprising a noble metal having a porous structure through which the at least one selected gas permeates, to the interface, and interacts at the interface with the noble metal and the at least one selected metal of the metal substrate to produce the at least one corresponding corrosion product, the corrosion products having respective, characteristic colors, different from each other and from an initial color of the test piece prior to being placed in the environment, in accordance with the at least one selected metal of the metal substrate and each gas of the group.

2. The environment monitoring test piece according to claim 1, wherein said metal thin-film has a thickness of 400 nm or less.

3. The environment monitoring test piece according to claim 2, wherein said metal thin-film has a thickness of 20–400 nm.

4. The environment monitoring test piece according to claim 3, wherein said metal thin-film has a thickness in the range of 100–200 nm.

5. An environment monitoring test piece, comprising:
   a layered structure comprising a metal thin-film formed on a metal substrate and defining an interface therebetween, which test piece is to be placed in an environment to be measured thereby to selectively determine the approximate amount of at least one gas, selected from the group consisting of $NO_x$, $SO_x$, and $NH_3$, in the environment based on at least one corresponding corrosion product resulting from the interaction of said selected gas from the environment with said test piece after a prescribed period;
   said metal substrate comprises Cu;
   said metal thin-film comprises Ag having a porous structure through which the at least one selected gas permeates, to the interface and interacts at the interface with the noble metal and the at least one selected metal of the metal substrate to produce the at least one corresponding corrosion product, the corrosion products having respective, characteristic colors, different from each other and from an initial color of the test piece prior to being placed in the environment, in accordance with the at least one selected metal of the metal substrate and each gas of the group.

6. The environment monitoring test piece according to claim 5, wherein the noble metal thin-film has a porosity as defined by vacuum deposition of the noble metal.

7. The environment monitoring test piece according to claim 5, wherein the noble metal thin-film has a porous structure and is permeable to said at least one selected gas which thereby permeates through the noble metal thin-film to the interface.

8. An environment monitoring test piece, comprising:
   a layered structure comprising a metal thin-film formed on a metal substrate and defining an interface therebetween, which test piece is to be placed in an environment to be measured thereby to selectively determine the approximate amount of at least one gas, selected from the group consisting of $NO_x$, $SO_x$, and $NH_3$, in the environment based on at least one corrosion product resulting from the interaction of said selected gas from the environment with said test piece after a prescribed period;
   said metal substrate comprises Zn;
   said metal thin-film comprises Au having a porous structure through which the at least one selected gas permeates, to the interface and interacts at the interface with the nobel metal and the at least one selected metal of the metal substrate to produce the at least one corresponding corrosion product, the corrosion products having respective characteristic colors, different from each other and from an initial color of the test piece prior to being placed in the environment, in accordance with the at least one selected metal of the metal substrate and each gas of the group.

9. The environment monitoring test piece according to claim 8, wherein the noble metal thin-film has a porosity as defined by vacuum deposition of the noble metal.

10. The environment monitoring test piece according to claim 8, wherein the noble metal thin-film has a porous structure and is permeable to said at least one selected gas which thereby permeates through the noble metal thin-film to the interface therebetween.

11. A method of monitoring for a presence of at least one gas selected from the group consisting of $NO_x$, $SO_x$ and $NH_3$ gases in an environment, comprising:

preparing a test piece having a layered structure comprising a vacuum deposited thin-film on a metal substrate and defining an interface therewith, said metal thin-film comprising a noble metal having a porous structure and being permeable to the at least one selected gas which thereby permeates through the noble metal thin-film to the interface and, with water, produces a corresponding acid and said metal substrate comprising a metal which undergoes an electrochemical reaction with the acid, acting as an electrolyte, producing corresponding corrosion products of respective, different colors, as a function of a selected type of the nobel metal and a selected metal of the metal substrate for respective, different gases of the group; and placing the test piece in the environment to be measured thereby, for selectively determining an approximate amount of the at least one selected gas in the environment by examining a color of each corresponding corrosion product resulting from the interaction of said at least one selected gas in the environment with said test piece after a prescribed period.

12. The method according to claim 11, wherein said test piece is prepared by vacuum-depositing an Ag thin-film on a Cu substrate.

13. The method according to claim 11, wherein said test piece is prepared by vacuum-depositing an Au thin-film on a Zn substrate.

14. A method of testing a gaseous environment for selectively identifying a presence therein of at least one specific harmful gas, of a class of harmful gases, comprising the steps of:

placing a test piece in the environment, the test piece corresponding to the at least one specific harmful gas to be selectively identified and comprising a multi-layer structure of a substrate comprising a selected base material and a thin-film of a selected noble metal different from the base material and forming an interface with the substrate, the base material being selected from the class of metals and metal alloys acting as a cathode, and the noble metal being selected from the class of noble metals acting as an anode together with the base material, in an electrochemical reaction wherein the corresponding at least one specific harmful gas, mixed with water, acts as an electrolyte and, together, produce at least one corresponding corrosion product of a characteristic color respectively identifying the at least one specific harmful gas, of the class of harmful gases, present in the tested environment; and analyzing the change in color at the interface of the test piece from an original color thereof, prior to being placed in the environment, to the characteristic color, for selectively determining the identity of the at least one specific harmful gas.

15. A method of testing as recited in claim 14, further comprising analyzing the quantitative presence of each identified specific harmful gas, in accordance with the shading of the characteristic color and as a function of time.

16. A method of testing as recited in claim 14, further comprising determining the identification of the at least one harmful gas by visual observation of the characteristic color.

17. A method of testing as recited in claim 14, further comprising determining the identification of the harmful gas by analyzing the corrosion products by Fourier Transform Infrared Spectroscopy Reflection Absorption Spectroscopy.

18. A test piece for selectively identifying a presence in a gaseous environment of at least one specific harmful gas, of a class of harmful gases, comprising:

a multi-layer structure of a substrate comprising a selected base material and a thin-film of a selected noble metal, different from the base material and forming an interface with the substrate, the base material being selected from the class of metals and metal alloys acting as a cathode, and the noble metal being selected from the class of noble metals acting as an anode together with the base material, in an electrochemical reaction wherein the corresponding at least one specific harmful gas, mixing with water, acts as an electrolyte and, together, produce at least one corresponding corrosion product of a characteristic color respectively identifying the at least one specific harmful gas, of the class of harmful gases, present in the tested environment; and the test piece undergoing a change in color, from an original color thereof, prior to being placed in the environment, to the characteristic color of the corrosion product, as a result of the electrochemical reaction and, in accordance with the characteristic color, selectively identifying the at least one specific harmful gas.

* * * * *

UNITED STATES PATENT AND TRADEMARK OFFICE
CERTIFICATE OF CORRECTION

PATENT NO. : 5,750,406
DATED : May 12, 1998
INVENTOR(S) : Eiichi Nakajima, et. al.

It is certified that error appears in the above-identified patent and that said Letters Patent is hereby corrected as shown below:

Column 4, line 17, change "i.e., approximate" to (i.e., approximate) --.

Signed and Sealed this

Twelfth Day of January, 1999

Attest:

Attesting Officer     *Acting Commissioner of Patents and Trademarks*

UNITED STATES PATENT AND TRADEMARK OFFICE
CERTIFICATE OF CORRECTION

PATENT NO.: 5,750,406
DATED : May 12, 1998
INVENTOR(S): Eiichi NAKAJIMA et al.

It is certified that error appears in the above-identified patent and that said Letters Patent is hereby corrected as shown below:

Title Page, please insert the missing priority information as follows:

4-046897    03/04/92    Japan
    4-217069    08/17/92    Japan
    5-104524    04/30/93    Japan Col. 4,    line 17, change "i.e., approximate" to --(i.e., approximate)--.

Col. 8,    line 56, after "interface" insert --,--;
           line 60, after "respective" insert --,--.

Signed and Sealed this

Eighteenth Day of May, 1999

Attest:

Q. TODD DICKINSON

*Attesting Officer*    *Acting Commissioner of Patents and Trademarks*